United States Patent [19]

Wauchope

[11] Patent Number: 5,403,187

[45] Date of Patent: Apr. 4, 1995

[54] METHODS OF PREPARATION OF A TOOTH BY REDUCTION THEREOF

[76] Inventor: Frederick T. Wauchope, 75 Onaway Rd., Mississauga, Ontario, Canada, L5G 1A5

[21] Appl. No.: 190,486

[22] Filed: Feb. 2, 1994

Related U.S. Application Data

[63] Continuation-in-part of Ser. No. 162,958, Dec. 8, 1993, which is a continuation-in-part of Ser. No. 888,219, May 26, 1992, Pat. No. D 351,654.

[51] Int. Cl.⁶ ............................................. A61C 5/00
[52] U.S. Cl. .................................... 433/215; 433/166; 433/218
[58] Field of Search ............... 433/165, 166, 215, 223, 433/218, 219

[56] References Cited

U.S. PATENT DOCUMENTS 4,992,049  2/1991  Weissman ........................... 433/218

OTHER PUBLICATIONS

Majchrowicz, DMD, Mike, "Quality Control for Successful Crown and Bridge", *Dentistry Today*, May 1993.
Dale, DMD, Barry G. et al, "Tooth Preparation Outline Form" *Dentistry Today*, May 1993.
Farah, John W., "Porcelain Inlays and Outlays: Why, When and How", *Dentistry Today*, May 1993.
*Fundamentals of Fixed Prosthodontics*, Quintessence Publishing Co., Chapter 3, "Preparation for Full Veneer Crowns", pp. 115–122.
Martignoni, M. et al., "Positioning the Crown Margin", *Precision Fixed Prosthodontics Clinical and Laboratory Aspects*, Quintessence Publishing Co, 1990, pp. 74–94.

*Primary Examiner*—Cary E. O'Connor
*Attorney, Agent, or Firm*—Donald E. Hewson

[57] ABSTRACT

Methods of preparation of a tooth by reduction thereof are provided, so as to permit very accurate tooth reduction in preparation for subsequent placement of a crown, onlay, inlay, or other crown or bridge prosthodontic procedure. Such preparation requires that at least a portion of the material of the tooth, its enamel and/or dentin, is to be reduced; and in order to do so, a series of grooves must first be cut into the tooth structure to a specific and predetermined depth. By the present invention, the depth of tooth reduction to be effected is determined, and a dental burr is chosen to cut a series of grooves each having that predetermined depth. After the series of groove reduction have been cut, the cut groove reductions are then connected using a suitable grinding burr so as to grind away the standing enamel and/or dentin lands between the grooves reductions and thereby achieve a reduction of the tooth structure to that predetermined depth. The depth of cut of each groove reduction, once determined, is achieved by using a dental burr that has a cutting projection that extends beyond a shoulder formed along the axial length of the dental burr, which cutting projection has a cutting surface on its outer periphery that can cut into the enamel and/or dentin of a tooth. Thus, when a groove is cut and the cutting projection extends into the tooth structure, the shoulder will impinge upon the surface of the tooth structure at each side of the groove being cut, and thereby preclude further depth advancement of the dental burr beyond the predetermined depth. The preparation steps may also be used for onlay or inlay procedures to reduce and cover or encapsulate existing silver amalgam material already in place in the tooth structure.

3 Claims, 1 Drawing Sheet

METHODS OF PREPARATION OF A TOOTH BY REDUCTION THEREOF

This application is a continuation-in-part application of U.S. patent application Ser. No. 08/162,958, filed Dec. 8, 1993, pending; which is a continuation-in-part application of U. S. patent application Ser. No. 888,219, filed May 26, 1982, now U.S. Pat. No. 0,351,654.

FIELD OF THE INVENTION

This invention relates to the preparation of a tooth or teeth by cutting tools that are used by dentists for cutting into and removing material of the tooth, especially the enamel and dentin thereof. The methods of the present invention is particularly directed to the use of dental burrs that are particularly intended for use in the preparation of a tooth for subsequent placement of a crown, or inlay, onlay, veneer, or other crown or bridge prosthodontic procedure, where it is required to reduce the surface of the tooth, or at least a portion of the surface of the tooth, by a specified amount. By reducing the surface of the tooth it is meant that a portion of the tooth is ground off, to be replaced by an artificial material.

BACKGROUND OF THE INVENTION

Dental procedures have, for many years, involved several distinct kinds of surgical operations with differing purposes and effects. For example, dental procedures that most people undergo involve the removal from the tooth of a small portion thereof so as to remove dental caries that are effecting that tooth. The dental caries and at least a small portion of healthy tooth surrounding it are removed, the preparation that is thus produced is then ready to accept a filling, and the filling is then placed. A variety of drilling or cutting instruments are employed during such a procedure.

Another procedure that is not so common, but nonetheless may be practised by an ordinary family dentist at least several times each week during the conduct of his business, is the preparation of a tooth or teeth for subsequent placement of crowns, onlays, inlays, or veneers. Another related procedure is the precise preparation of a tooth to accommodate a clasp or rest of prescribed dimensions for a removable partial denture. For purposes of this discussion, all such related procedures—the removal of the surface or at least a portion of the surface of the tooth to prepare it for subsequent placement of an artificial substance—will be considered as being in respect of dental crown preparation.

Briefly, dental crown preparation requires the dentist to grind or otherwise remove a specific amount of the surface of the tooth. This procedure, reduction of the tooth, generally requires that the depth or amount of reduction shall be from about 0.5 mm to about 2.0 mm. This is not to say that the amount of reduction should vary on any one tooth in any one procedure—although that is possible; but it is to say that the amount of reduction may vary from tooth to tooth or procedure to procedure, depending on a number of circumstances that would be determined by the dentist at that time. Also, of course, the amount of reduction might be somewhat less for purposes of placement of an onlay or inlay, or possibly a veneer, as opposed to the amount of reduction that might be required for the placement of a crown or partial crown.

The dental procedures of grinding teeth, or cutting or abrading teeth, are generally carried out using rotationally driven cutting or grinding instruments, which in general might be classified as being dental burrs. In fact, the usual classification of armamentarium may comprise a variety of rotary instruments that might be specifically classified as stones, burrs, or drills. For example, the stones are used for abrading or wearing down the surface of the tooth such as by the use of fine diamond chips or dust that are cemented to a base. In a narrow definition, dental burrs may be considered to be miniature milling cutters, having a plurality of blades that shear away the tooth structure from the tooth surface and where the cutting blades are disposed along the sides of the instrument. Drills, specifically twist drills, have their cutting edges at the tips of the instrument, and are generally intended only so as to bore a small diameter hole into the tooth structure. However, for purposes of this discussion, all of the above instruments may be generally considered to be dental burrs, and this will be especially so in the following discussion which proposes several alternative surface treatments or geometries for dental burr structures that are otherwise in keeping with the present invention.

When dental crown preparation is being undertaken, the dentist first determines how much surface reduction should be made. Then, the portion of the tooth surface, if not the entire tooth surface, is marked so as to determine the boundaries within which the procedure will be undertaken if it is not over the entire surface of the tooth. Tooth reduction then begins, and it is at this point that dental burrs according to the present invention will be used.

When a crown procedure is being undertaken, the general steps include tooth reduction, and then an impression of the remaining tooth is taken and sent to a dental prosthetics laboratory. The laboratory then fabricates the crown, having made a model of the impression, and having been informed of the desired prosthesis type, they must assume that accurate reduction and/or preparation has been accomplished by the dentist to permit said prosthesis fabrication. In other words, the dental prosthetics laboratory has in its hands a model of the tooth after the reduction has been made, and it is then required to build a crown to be cemented to the remaining portion of the tooth and to restore the depth of reduction that has been prepared by the dentist. The crown is then fabricated and returned to the dentist for placement in the mouth, usually a few days or a week or so after the tooth reduction has been taken.

A more complete discussion of the dental burrs used in the initial, depth gauging steps of tooth reduction and crown preparation techniques and procedures, will be found in companion application Ser. No. 08/162,958, filed Dec. 8, 1993 in the name of the present inventor, and relating to DENTAL BURRS; of which application the present application is a C-I-P. Those dental burrs are the ones used in the most difficult step taken in crown preparation—that is the maintenance of a constant depth of reduction, once it has been determined as to how much reduction should occur. If the depth of reduction has not been constant, or has been more or less than advised by the prosthetic technical specifications, then the crown may not fit or it may not replicate the previous tooth structure which it replaces. The manner by which the depth of the reduction is to be determined may vary slightly among dentists, but not significantly. When a dentist is preparing the tooth for tooth reduction, he first cuts a series of grooves into the tooth. Almost invariably, the series of grooves is cut into the tooth using a long cutting burr that may be cylindrical, or which may be slightly tapered, but in any event the groove is cut into the surface of the tooth by placing the burr lengthwise against the tooth and pressing it into the tooth along the length of the burr while the burr is rotating. This creates a groove that is as long as the burr or at least the portion of the burr that is in contact with the surface of the tooth. But the depth of the groove is difficult to determine; and the usual practice is essentially to gauge the diameter of the burr and then sink the burr into the surface of the tooth for one-half of its diameter—or in some cases, its full diameter. After several grooves are placed into the surface of the tooth, then the remaining tooth material between the grooves is ground or abraded away, until the depth of the grinding or abrading of the material reaches the same depth as the grooves that have been previously cut into place by the side of a burr as noted above.

The steps preceding the cutting of a plurality of grooves into the surface of the tooth, and the steps of removing the tooth's structure between the grooves after they have been put in place, would remain essentially the same for any dentist who uses the dental burr of the present invention, as previously. However, the step of placing the grooves into the surface of the tooth, so as to determine the boundaries of the tooth reduction procedure if an entire reduction is not taking place and the placement of intermediate depth grooves where gross reduction is taking place, are easily and extremely accurately undertaken using the dental burr of the present invention. Of course, even when an entire crown is to be placed, meaning that the entire surface of the tooth is to be reduced, there still remains a boundary at the gingival area of the tooth, where the shoulder of the crown to be placed meets the remaining structure of the tooth at, near, or below the gumline.

What the present invention provides is a dental burr whose purpose is to cut a groove into the tooth structure, where the groove has a specific and predetermined depth. As noted above, the depth of the groove to be cut into the tooth may only be as little as 0.5 mm in some cases, or it may be as much as 2.0 mm in other cases. Also, as noted above, the depth of the groove should be uniform, because the dental prosthetics laboratory assumes that a constant depth of reduction has occurred over prescribed tooth areas for which the laboratory is fabricating the crown or other dental prosthetic.

There are, of course, several reasons for the concern as to the accuracy of the depth of the grooves that are initially placed in the tooth structure as part of the dental crown procedure. They include among them the fact that, if the depth of the groove is either too much or too little, then the dental prosthetic that has been prepared by the laboratory may not fit—in that it would not necessarily replicate the tooth structure that it replaces. If less reduction has occurred than the respective restorative dentistry specifications dictate, then it is possible that a crown might not go into place because its resultant laboratory fabrication would be overcontoured and thereby interfere with the adjacent tooth or teeth. If more reduction has occurred than has been prescribed by restorative dentistry specifications, then the vitality of the tooth may be jeopardized by the stated over-reduction.

It should be noted that, a final impression is only made after the reduction procedure has taken place. Preliminary impressions that are made prior to the tooth reduction procedure are taken in order to mould a temporary crown or restoration that is put into place for cosmetic and functional purposes, which crown or restoration is generally one that is fabricated by the dentist in his own office.

Of course, if the tooth reduction has been inaccurately done, then unhappiness may occur between the patient and the dentist, and/or between the dentist and the dental prosthetic laboratory. This could mean unwarranted and unnecessary delays in time, additional time in the chair by the patient—for which the patient may be quite unwilling to pay the dentist—and sometimes it may require re-fabricating the dental prosthetic, the cost for which may have to be absorbed by the dentist or the laboratory. When the depth of the initial depth gauge grooves are accurately determined and placed, then none of the above difficulties would arise.

A further purpose to which the methods of the present invention may be put is the preparation of onlay or inlay to cover or encapsulate existing silver amalgam that is already in place in a tooth structure. Recently, there has been some concern raised about the mercury component of silver-amalgam—a material that has been used over a long period of time as fillings in teeth after removal of dental caries—becoming systemic within the body of the patient. By employing the present invention, the existing silver-amalgam can be reduced a sufficient amount that an enamel, gold, or other dental material onlay or inlay may be emplaced. The chance of mercury release and/or chelation into the body of the patient has been shown to be much greater due to grinding, attrition, or fracture of the silver-amalgam filling, and escape of mercury into the mouth, than the likelihood of mercury becoming systemic in the body of the patient through the root structure of the tooth. Thus, conventional onlay or inlay techniques may be employed to cover or encapsulate the remaining silver-amalgam after reduction; and it is evident that reduction using the process and methods of the present invention ensures an economical and effective onlay or inlay. Indeed, as at the filing date of this Application, silver-amalgam restorations are not allowed in Sweden. Thus, the methods of the present invention can be used to define and remove a portion of the silver-amalgam restoration from a tooth, so that no trauma is caused to the otherwise healthy tooth.

DISCUSSION OF PRIOR ART

Apart from the professional experiences of practising dentists, whose experience would be individual in each instance, there are a number of professional references, articles written by practising dentists, and text books, that discuss the techniques and principles surrounding crown preparation.

For example, there are several references in the May 1993 edition of DENTISTRY TODAY, that discuss several issues that are of particular concern, and over which the present invention provides an advance and improvement. One article, by Mike Majchrowicz, a practising dentist who has also worked as a laboratory technician in dental prosthetic laboratories, discusses the importance of uniform tooth reduction for adequate strength and aesthetics, particularly when directed to porcelain crowns. Dr. Majchrowicz has noted that often, crowns are approximately 20% larger than the original tooth diameter because of overcontouring or inadequate tooth reduction. In other words, the dentist has informed the laboratory that he has accomplished tooth reduction in a given amount, and it turns out that he has not, resulting in a cast crown that has too much material in it.

Another article in the same magazine by Dale and Aschheim is particularly directed to the problems of incisal reduction, where about 1 mm of porcelain thickness should be allowed for. The article discusses the problem of butt joint finishing, noting that after ideal tooth preparation, the incisal outline of the tooth when viewed from the labial aspect, should be identical to the incisal outline of the proposed final restoration—except for the 1 mm reduction.

Yet a further article by John W. Farah emphasizes the importance that, for example when the tooth is to be prepared for a gold inlay or onlay, that the tooth should not be bevelled but that the depth of the inlay should be about 2 mm.

None of the articles, however, discusses how the depth of reduction should be governed and adequately controlled, and the assumption is made that all of those authors are directing their comments to dentists who generally function in the usual manner by first using armamentarium that comprises a straight or slightly tapered burr, and sinking the burr into the tooth structure for part of the burr diameter up to or exceeding its full diameter, so as to establish the depth gauge groove.

The text book FUNDAMENTALS OF FIXED PROSTHODONTICS, second edition, published in 1981 by Quintessence Publishing Co. Inc., edited by Shillingberg, Hobo, and Witset, discusses the armamentarium necessary, for example, for a full veneer crown. It is suggested, at pages 115–117, that occlusal reduction should occur in the amount of about 1.5 mm on the functional cusps and about 1.0 mm on the non-functional cusps. This text book suggests that depth orientation grooves should be placed on the occlusal surface of the tooth to provide an easy reference to determine when sufficient reduction has been done, because if the orientation marks are not made there will be time wasted in repeated checks for adequate clearance. The depth orientation grooves are suggested to be placed using a taper fissure burr or a round-end tapered diamond, with the grooves being cut by placing the burr against the tooth and cutting into the surface of the tooth structure along the length of the burr. Likewise, at pages 119 and 122, the text book suggests that for porcelain fused to metal crowns, the depth orientation grooves should be placed on the labial and incisal surfaces with a flat-end tapered diamond, with the grooves being formed into the surface of the tooth to a depth of about 1.2 mm. The placing of the depth orientation grooves using a flat-end tapered diamond is illustrated, from which it is very clear that the depth orientation grooves cannot accommodate or follow the curvature of the tooth. Porcelain jacket crowns require depth orientation grooves placed in the same manner, the depth of which is 1.0 mm on the labial and 2.0 mm deep on the incisal surfaces of the tooth. Once again, this text book suggests that the depth orientation grooves are merely placed using a flat-end tapered diamond which is forced along its length into the surface of the tooth structure.

Yet another text book, PRECISION FIXED PROSTHODONTICS, CLINICAL AND LABORATORY ASPECTS, published in 1990 by Quintessence Publishing Co. Inc., edited by Martignoni and Schönenberger, with translation to English, suggests at page 74 that the depth of cut should be obtained and controlled by utilizing a slightly tapered cutting instrument having a thickness of 2 mm, for example, and if the cutting instrument has a taper of between 4° and 6°, an efficient means is provided for high precision control simply by sinking the instrument to a depth of one-half of its diameter into the tooth.

Finally, the 1988 text book FUNDAMENTALS OF TOOTH PREPARATIONS, published by Quintessence Publishing Co. Inc., and edited by Shillingburg, Jacobi and Brackett, discusses various rotary instruments used in the armamentarium for purposes of tooth preparation, tooth structure reduction, drilling, etc. At pages 83–86 of that text book, there again is provided a description of tooth reduction for purposes of full veneer crowns. Specifically, the suggestion is made that to achieve a desired occlusal reduction, depth orientation grooves should be cut using a round-end tapered diamond drill, and that the depth of the groove can be gauged from the diameter of the diamond drill used for the reduction. The text also suggests that an enamel chisel having a specific width can also be used by placing it in the depth-orientation groove being cut, to determine if the depth of the groove has yet reached the width of the chisel—which is generally either 1.0 mm or 1.5 mm. Further preparation for anterior porcelain fused to metal crowns is discussed at pages 260–264, and once again the depth-orientation grooves are placed in the tooth using a flat-end tapered diamond drill. Indeed, in this instance, the suggestion is made to sink the cutting tool into the surface of the tooth to the full diameter of the tool, whereby the depth of the groove is then determined as a function of the diameter of the diamond faced rotary tool being used.

From all of the above, it is seen that the standard and approved method of determining the depth of grooves to be formed in the tooth to establish the boundaries of the area to be subjected to tooth reduction, or to establish gauges by which overall tooth reduction can be achieved using diamond wheels and the like to remove the lands formed in the tooth structure between the grooves when the grooves have been made, always requires the use of a straight or slightly tapered instrument where the depth of the groove is determined by sinking the cutting instrument into the surface of the tooth structure either to part of its diameter or fully to its diameter. However, this means that in all cases that the depth-orientation groove being formed has a straight line surface which does not follow the contour of the tooth. Severe difficulties can thereafter occur because of the fact that the contour of the tooth must then be guessed at by the technicians who are manufacturing the cast dental prosthetic to be placed onto the tooth.

THE ARMAMENTARIUM FOR THE PRESENT INVENTION

The present inventor provides a dental burr by which the methods of the present invention can be carried out. That dental burr is described in detail in the companion application entitled DENTAL BURR, noted above. In brief, the dental burr to be utilized in performing the methods of the present invention comprises a body that has a stem adapted for placement at a first end thereof into a driving implement or hand piece, so as to impart rotational driving force to the dental burr. A cutting projection is formed at the second or distal end of the body, and the cutting projection is substantially cylindrical but has a cutting surface on its outer periphery—where the cutting surface may be cutting grooves or a grinding or abrading surface. There is an intermediate portion of the body of the dental burr that is axially located between the first end and the second end of the burr, which is generally cylindrical and which has a diameter that is greater than the diameter of the cutting projection that extends beyond it. The cylindrical intermediate portion terminates in a shoulder, beyond which the cutting projection of the dental burr extends, and the shoulder is substantially planar and projects radially outwardly from the cutting projection. The length of the cutting projection beyond the shoulder is of a predetermined and specific length.

Obviously, use of a dental burr as that described above will accomplish the cutting of grooves into the tooth of a precise and specific depth. By using dental burrs having different lengths of cutting projection, different depth grooves can be cut into the tooth structure.

THE INVENTION

By using the armamentarium described above the present invention provides a method of preparation of a tooth by reduction thereof for subsequent placement of a crown or inlay, or other crown or bridge prosthodontic procedure. During that tooth reduction procedure, at least a portion of the enamel and/or dentin of the tooth is to be reduced, and the present invention provides for the steps of:

(a) determining the depth of tooth reduction to be effected;
(b) choosing a dental burr to cut a series of grooves, each having a predetermined depth, into the tooth enamel and/or dentin at least at the boundaries of at least a portion of the tooth surface which is to be subjected to tooth reduction, and also intermediately of the grooves formed at the boundaries of the at least a portion of the tooth surface, if necessary;
(c) cutting a series of grooves or reductions using the chosen dental burr, which is rotationally driven in a suitable driving implement, and thereby creating a number of standing enamel and/or dentin lands in the tooth structure between the grooves, which standing lands are defined by the grooves; and
(d) connecting the cut groove reductions with a suitable grinding burr, by grinding the standing lands of tooth enamel and/or dentin between the groove reductions so as to reduce those lands to the same depth as the groove reductions, and thereby so as to effect a reduction of the at least a portion of the tooth enamel over its entire area to the determined depth.

As indicated above, the depth of cut each groove reduction, once determined, is achieved in keeping with the present invention by the chosen dental burr having a cutting projection which extends beyond a shoulder formed along the axial length of the dental burr. The outer periphery of the cutting projection is formed with a cutting or grinding or abrading surface so as to cut into the tooth structure. Thus, when a groove is cut and the cutting projection extends into the dental enamel and/or dentin, the shoulder of the dental burr will impinge upon the surface of the tooth enamel and/or dentin at each side of the groove being cut, and thus further depth advancement of the dental burr beyond the determined depth is thereby precluded.

OBJECTS OF THE INVENTION

It is therefore an object of the present invention to provide methods whereby tooth preparation by reduction, for subsequent placement of a crown or inlay, or other crown or bridge prosthodontic procedure, may be achieved, using a dental burr whose structure is such that the depth-orientation grooves formed by the dental burr are of a precise and predetermined depth.

According to particular applications of the present invention, tooth structure at the gingival junction can be reduced in various configurations. Included among them may be various margins that are chamfered or have a stepped-chamfer, or a bevelled shoulder.

BRIEF DESCRIPTION OF THE DRAWINGS

The present invention will be described in greater detail hereafter, in association with the accompanying drawings which are provided for purposes of example only and in which.

DESCRIPTION OF THE PREFERRED EMBODIMENTS

Figure 1:
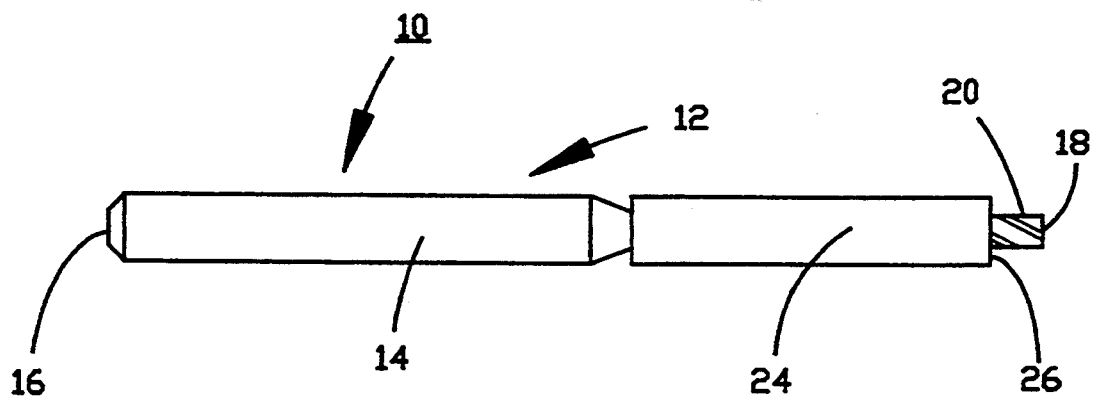
FIG. 1 shows a typical dental burr which is used for carrying out the method of the present invention.

First, having regard to FIG. 1, a typical dental burr 10 which is used for carrying out the methods of this invention comprises a body 12, having a stem 14 which is located at the first end 16 of the dental burr. At the second end 18 of the dental burr there is a cutting projection 20, behind which is located an intermediate portion 24 which has a greater diameter than the diameter of the cutting projection 20. The intermediate portion 24 terminates at a shoulder 26, beyond which the cutting projection 20 extends, and the shoulder 26 extends radially outwardly from the cutting projection 20 and is planar.

In carrying out the methods of preparation of the tooth, for tooth reduction purposes, by cutting a series of grooves into the tooth, it is first determined where the grooves should be cut if they are to define the outer boundaries of at least a portion of the tooth to be reduced. Of course, it is important that the depth of the grooves be determined.

Figure 2:
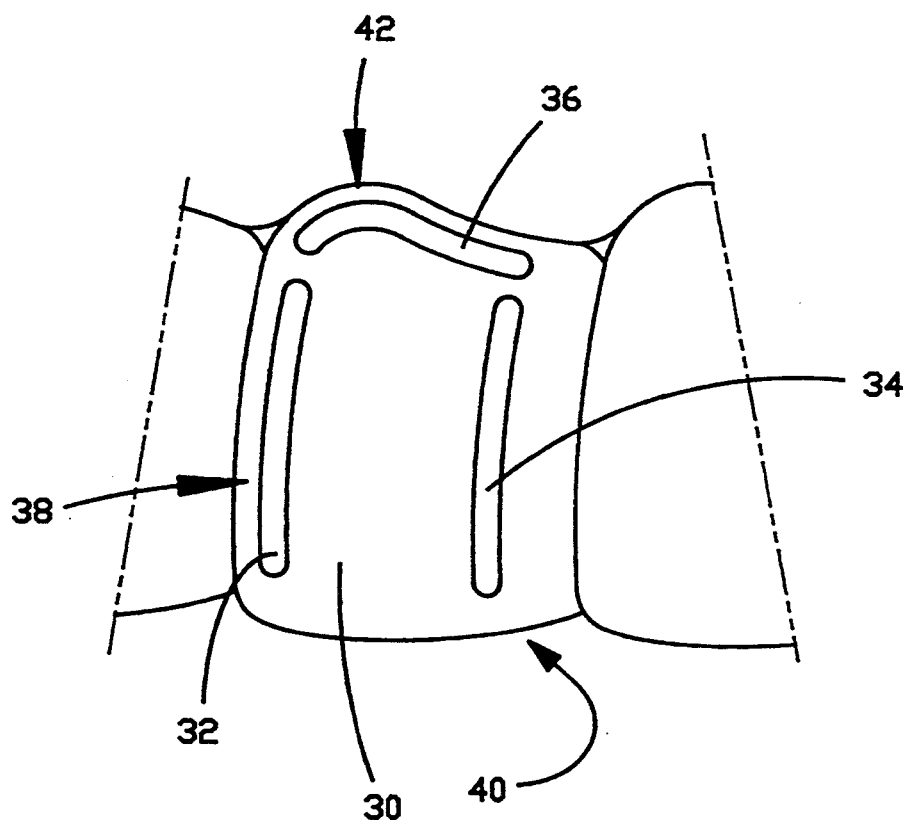
FIG. 2 shows the manner in which several grooves might be placed in a tooth in keeping with the methods of the present invention.

With reference to FIG. 2, a typical tooth 30 is shown, into which three grooves, 32, 34, and 36 have been cut. In this case, the grooves 32 and 34 are apparently cut into the labial surface of the tooth 30, indicated generally at 38. Similar grooves may also be cut into the lingual surface of the tooth 30, shown by 40, if the total surface of the tooth is to be reduced. The groove 36 is cut generally near the gingival portion of the tooth, the margin of which is shown at 42.

Several of the crown or inlay, bridge prosthodontic, or other procedures that may be carried out according to the methods of the present invention include the placement of full metal crowns, porcelain or porcelain jacket crowns, porcelain fused to metal crowns, acrylic crowns, metal and/or porcelain inlays and/or onlays, porcelain veneers, acrylic veneers, or the preparation of exact rest seat areas in a tooth for the preparation of a removable denture.

As pointed out in the Majchrowicz article, noted above, exact reductions are called for in the preparation of proper crown, inlay, onlay, veneer, or rest preparations, due to the requirement of uniform reduction of the tooth. Failure of uniform reduction affects the quality control. Moreover, exact and predetermined configurations for finished margin and the outline of the tooth are important, as discussed in several of the references such as the Dale et al reference and the Farah reference, noted above.

Thus, the methods of the present invention permit and provide for precise extension of reduction into the proximal sub-contact area of adjacent teeth, by permitting a predetermination of the depth of the groove to be cut. Moreover, since the dental burr may be placed against the tooth in a manner that is perpendicular to the tooth surface, rather than parallel to it, more exact placement of the groove may achieved.

A study has been made by the present inventor, having regard to conventional techniques, both as to the number of procedural steps to be taken, and the amount of time taken for such preparation. Moreover, the experience of the present inventor has shown that because the dental prosthetic laboratory can be assured of the precise amount of reduction that has occurred, both the dentist and the laboratory can have the satisfaction that its prosthetic will fit correctly and appropriately at the first fitting when the patient has returned to the dentist for that fitting.

When a full tooth reduction is to be made, then the cutting steps that may occur may comprise the following five steps:

i) a single occlusal reduction;
ii) a single lingual or palatal axial reduction;
iii) a single buccal or labial axial reduction;
iv) a pair of proximal shoulder reductions; and
v) a gingival reduction to establish a margin, chamfer, or shoulder which may be bevelled or stepped.

The above steps are in contrast to the at least nine cutting steps that would be required if the depth-orientation grooves were to be cut using ordinary procedures, where a cutting instrument is placed parallel to the surface of the tooth to cut a groove therein.

By the above, the present invention provides methods for preparation of a tooth by reduction thereof, where the tooth reduction is prior to and in contemplation of subsequent placement of a crown or inlay, or other crown or bridge prosthodontic. The present invention calls for use of a dental burr which is specifically defined so as to have a cutting projection that extends beyond a shoulder, whereby the shoulder will impinge upon the surface of the tooth enamel when the dental burr is held substantially perpendicularly to the surface of the tooth, thus accurately controlling the depth of the cut.

The scope of the present invention is defined by the accompanying claims.

I claim:

1. A method of preparation of a tooth by reduction thereof for subsequent placement of a crown, onlay, inlay, or other crown or bridge prosthodontic procedure, wherein at least a portion of the material of the tooth, its enamel and/or dentin and/or previous silver-amalgam restoration, is to be reduced, comprising the steps of:
   (a) determining the depth of tooth reduction to be effected;
   (b) choosing a dental burr to cm a series of grooves, each having a predetermined depth, into the material of the tooth structure at the enamel and/or dentin and/or previous silver-amalgam restoration thereof at least at the boundaries of the at least a portion of the tooth surface, and intermediately if necessary;
   (c) cutting a series of groove reductions using the chosen dental burr which is rotationally driven in a suitable driving implement and thereby creating a number of standing enamel lands between said grooves and defined thereby; and
   (d) connecting the cut groove reductions with a suitable grinding burr by grinding the standing enamel and/or dentin lands between the groove reductions so as to reduce the lands to the same depth as the groove reductions, and thereby so as to effect a reduction of the at least a portion of the tooth enamel and/or dentin to the determined depth;
   wherein the depth of cut of each groove reduction, once determined, is achieved by the chosen dental burr having a generally cylindrical cutting projection which extends beyond a shoulder formed along the axial length of the dental burr, said cutting projection having a cutting surface on the outer periphery thereof that can cut into the enamel and/or dentin of a tooth; whereby, when a groove is cut and said cutting projection extends into said dental enamel and/or dentin, said shoulder will impinge upon the surface of the tooth structure at each side of the groove being cut, and thereby preclude further depth advancement of the dental burr beyond the predetermined depth; and wherein:
   step (c) comprises the following cutting steps:
      (i) a single occlusal reduction;
      (ii) a single lingual or palatal axial reduction;
      (iii) a single buccal or labial axial reduction;
      (iv) a pair of proximal shoulder reductions; and
      (v) a gingival reduction to establish a margin, chamfer, or shoulder.

2. The method of claim 1, wherein the margin, chamfer or shoulder that is established in step (c)(v) is bevelled.

3. The method of claim 1, wherein the margin, chamfer or shoulder that is established in step (c)(v) is stepped.

* * * * *